United States Patent
Lee et al.

(10) Patent No.: US 11,403,791 B2
(45) Date of Patent: Aug. 2, 2022

(54) APPARATUS AND METHOD USING DEEP LEARNING (DL) TO IMPROVE ANALYTICAL TOMOGRAPHIC IMAGE RECONSTRUCTION

(71) Applicant: CANON MEDICAL SYSTEMS CORPORATION, Otawara (JP)

(72) Inventors: Tzu-Cheng Lee, Vernon Hills, IL (US); Jian Zhou, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/509,429

(22) Filed: Jul. 11, 2019

(65) Prior Publication Data
US 2021/0012541 A1   Jan. 14, 2021

(51) Int. Cl.
| | | |
|---|---|---|
| *G06K 9/00* | (2022.01) | |
| *G06T 11/00* | (2006.01) | |
| *G06T 5/20* | (2006.01) | |
| *G06T 5/00* | (2006.01) | |

(Continued)

(52) U.S. Cl.
CPC ............ *G06T 11/006* (2013.01); *A61B 6/032* (2013.01); *A61B 6/037* (2013.01); *G01N 23/046* (2013.01); *G06T 5/002* (2013.01); *G06T 5/20* (2013.01); *G06T 11/005* (2013.01); *G01N 2223/401* (2013.01); *G06T 2207/10081* (2013.01); *G06T 2207/10104* (2013.01); *G06T 2207/10108* (2013.01); *G06T 2207/10121* (2013.01); *G06T 2207/20081* (2013.01); *G06T 2207/20084* (2013.01); *G06T 2207/30004* (2013.01); *G06T 2210/41* (2013.01); *G06T 2211/421* (2013.01)

(58) Field of Classification Search
CPC ......... G06T 11/006; G06T 5/002; G06T 5/20; G06T 11/005; G06T 2207/10081; G06T 2207/10104; G06T 2207/10108; G06T 2207/10121; G06T 2207/20081; G06T 2207/20084; G06T 2207/30004; G06T 2210/41; G06T 2211/421; A61B 6/032; A61B 6/037; G01N 23/046; G01N 2223/401
See application file for complete search history.

(56) References Cited

U.S. PATENT DOCUMENTS

| | | |
|---|---|---|
| 2014/0119628 A1 | 5/2014 | Elad et al. |
| 2018/0293762 A1 | 10/2018 | Fu et al. |
| 2019/0035116 A1* | 1/2019 | Xing ........................ G06T 5/002 |

(Continued)

OTHER PUBLICATIONS

Andrew Web, "Introduction to Biomedical Imaging", Hoboken, N.J. : Wiley-Interscience, © 2003. Wiley-IEEE Press. IEEE Press series in biomedical engineering. pp. 238 and 239 (Year: 2003).*

(Continued)

*Primary Examiner* — Atiba O Fitzpatrick
(74) *Attorney, Agent, or Firm* — Oblon, McClelland, Maier & Neustadt, L.L.P.

(57) ABSTRACT

A method and apparatus is provided to improve the image quality of images generated by analytical reconstruction of a computed tomography (CT) image. This improved image quality results from a deep learning (DL) network that is used to filter a sinogram before back projection but after the sinogram has been filtered using a ramp filter or other reconstruction kernel.

20 Claims, 9 Drawing Sheets

(51) Int. Cl.
*G01N 23/046* (2018.01)
*A61B 6/03* (2006.01)

(56) References Cited

U.S. PATENT DOCUMENTS

2019/0035118 A1  1/2019  Zhao et al.
2020/0043204 A1* 2/2020  Fu ..................... G06N 3/0454

OTHER PUBLICATIONS

Dong Hye Ye, et al. "Deep Back Projection For Sparse-View CT Reconstruction"; School of Electrical and Computer Engineering—Department of Mathematics, Purdue University, West Lafayette, IN, 47907; arXiv:1807.02370v1; [eess.IV] Jul. 6, 2018.

Hu Chen, et al. "Low-Dose CT via Deep Neural Network"; College of Computer Science, Sichuan University, Chengdu 610065, China, National Key Laboratory of Fundamental Science on Synthetic Vision, Sichuan University; Chengdu 610065, China, 1 Department of Scientific Research and Education, The Sixth People's Hospital of Chengdu; Chengdu 610065, China, Department of Biomedical Engineering, Rensselaer Polytechnic Institute, Troy, NY 12180, USA; 9 pages.

Jiang Hsieh. "Computed Tomography Principles, Design, Artifacts, and Recent Advance" 2nd edition, SPIE 2009.

Gengsheng L. Zeng, et al. "Revisit of the Ramp Filter" IEEE Trans Nucl Sci. 2015; 62(1): 131-136; pp. 1-14.

Qingsong Yang, et al. "CT Image Denoising with Perceptive Deep Neural Networks"; The 14th International Meeting on Fully Three-Dimensional Image Reconstruction in Radiology and Nuclear Medicine; Jun. 2017; pp. 858-863.

Eunhee Kang, et al. "A Deep Convolutional Neural Network Using Directional Wavelets for Low-Dose X-ray CT Reconstruction"; Medical Physics 2017; 44(10): e360-e375; arXiv: 1610.09736v3 [cs.CV] Oct. 14, 2017.

Hu Chen, et al. "Low-Dose CT With a Residual Encoder-Decoder Convolutional Neural Network"; IEEE Trans Medical Imaging 2017; 36(12): 2524-2535.

Jiang Hsieh; "Adaptive Streak Artifact Reduction in Computed Tomography Resulting from Excessive X-Ray Photon Noise"; Medical Physics 1998; 25(11): 2139-2147.

Armando Manduca, et al. "Projection Space Denoising With Bilateral Filtering and CT Noise Modeling for Dose Reduction in CT"; Medical Physics 2009; 36(11): 4911-4919.

Andreas Maier, et al. "Three-Dimensional Anisotropic Adaptive Filtering of Projection Data for Noise Reduction in Cone Beam CT"; Medical Physics 2011; 38(11): 5896-5909.

Rushil Anirudh; et al. "Lose The Views: Limited Angle CT Reconstruction via Implicit Sinogram Completion"; arXiv.org 2017, arXiv:1711.10388; 6343-6352.

Hoyeon Lee, et al. "Deep-Neural-Network Based Sinogram Synthesis for Sparse-View CT Image Reconstruction"; arXiv.org 2018, arXiv:1803.00694.

* cited by examiner

APPARATUS AND METHOD USING DEEP LEARNING (DL) TO IMPROVE ANALYTICAL TOMOGRAPHIC IMAGE RECONSTRUCTION

FIELD

This disclosure relates to reconstruction of medical images in which a deep learning (DL) neural network is applied during an analytical reconstruction process (e.g., filtered back-projection), and, more particularly, the DL neural network is applied after the filtering step in which the sinogram is filtered using a reconstruction kernel (e.g., a ramp filter) and before the analytical reconstruction step (e.g., back-projection).

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

Medical imaging produces images of the internal members of a patient's body. Examples of medical-imaging modalities include: X-ray radiography, X-ray computed tomography (CT), positron emission tomography (PET), single-photon emission CT (SPECT), fluoroscopy, and angiography. Once the images have been produced, a physician can use the images to diagnose a patient's injuries or diseases X-ray CT systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

X-ray CT has found extensive clinical applications in cancer, heart, and brain imaging. As CT has been increasingly used for a variety of applications including, e.g., cancer screening and pediatric imaging, there has arisen a push to reduce the radiation dose of clinical CT scans to become as low as reasonably achievable. For low-dose CT, the image quality can be degraded by many factors, such as high quanta noise challenge scanning geometry.

Although many cutting-edge technologies have been developed to improve low-dose CT image quality, better methods (e.g., faster, more robust, and/or improved noise suppression) are desired to improve image quality, thereby enabling clinical quality images at increasingly lower X-ray doses.

BRIEF DESCRIPTION OF THE DRAWINGS

A more complete understanding of this disclosure is provided by reference to the following detailed description when considered in connection with the accompanying drawings, wherein.

DETAILED DESCRIPTION

As discussed above, better methods to improve image quality for analytical reconstruction of tomographic images are desired for many reasons. These reasons include that analytical reconstruction methods can be fast, and improving image quality can enable clinical image quality at lower radiation doses. Additionally, better methods can reduce artifacts and/or enhance resolution. The methods described herein provide improved performance though applying one or more deep learning networks during the filtering step of an analytical reconstruction method.

For example, filtered back-projection (FBP) is often used for analytical reconstruction of computed tomography (CT) images. FBP can be thought of as a filtering step together with an analytical reconstruction step. In the filtering step, a ramp filter (or other reconstruction kernel) is used to filter a sinogram. Then in the analytical reconstruction step, a CT image is generated by back-projecting the filtered sinogram. Generally, filtering (e.g., with the reconstruction kernel can be performed in either the spatial domain (e.g., by convolving the sinogram with the reconstruction kernel) or in the spatial-frequency domain (e.g., by respectively transforming the sinogram and the reconstruction kernel into the frequency domain and then multiplying). Herein, the term "spatial-frequency" while be abbreviated as "frequency." Further, the terms "projection domain" and "sinogram domain" are used to refer to the data prior to the analytical reconstruction step, and the term "image domain" refers to the data after the analytical reconstruction step.

Continuing with the example of FBP, the methods described herein apply a DL network after the filtering step and before the analytical reconstruction step. Further, in certain implementations, a second DL network can also be used prior to the filtering step to denoise the sinogram. This second DL can perform low-pass filtering or smoothing filtering, for example.

The reconstruction kernel (or filter) serves an important function of the analytic algorithm in CT image reconstruction. For example, the ramp filter in the data back projection process avoids blurring of the image. It is called a ramp filter because it looks like a ramp in the frequency domain. For example, the ramp filter is often applied by multiplying in the frequency domain by the factor of (i.e., proportional to the distance from zero frequency), in order to provide the correct analytical solution when back-projection is performed. Additional, the ramp filter can be multiplied by a window function that has been selected to provide a preferred noise texture and image contrast/resolution.

Compared to a related method, the methods described herein have several advantages. In the related method, a deep convolution neural network (DCNN) is applied to the sinogram to perform denoising and/or sinogram restoration only before (but not after) filtering the sinogram with the reconstruction kernel. By only applying a DCNN before the filtering step, the related method can under emphasize the importance and role of the high frequency components in the analytical reconstruction. This is better understood by considering that, for analytical reconstruction, the data has is filtered by the reconstruction kernel (e.g., the ramp filter) before back-projection, and the ramp filter applies a lower weight to the low-frequency components. The more heavily weighted frequency components, which are often the high-frequency components, play a greater role in the analytical reconstruction. The related method, which is performed prior to filtering by the reconstruction kernel fails take account for the greater weight applied to the high-frequency components, leading to inferior performance for analytical reconstruction.

Accordingly, in contrast to the related method, the methods described herein use a neural network in between the reconstruction-kernel filtering step and the analytical reconstruction step to account for the greater weights applied to the high-frequency components of the sinogram.

The methods described herein are primarily illustrated using the non-limiting example of X-ray CT as the imaging modality used to acquire the sinograms from which the CT images are reconstructed. However, the methods described herein can be used with other medical imaging modalities such as PET and SPECT, etc. by adapting the framework proposed herein. Accordingly, the discussion herein discloses and describes non-limiting examples of the present disclosure. As will be understood by those skilled in the art, the present disclosure may be embodied in other specific forms without departing from the spirit or essential characteristics thereof. Accordingly, the present disclosure is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

As discussed above, the methods described herein use a DL network (which can also be referred to as a neural network or an artificial neural network) that has been trained to optimize sinogram processing prior to an analytical reconstruction step (e.g., back projection). The illustrative examples discussed below often assume that the trained DL network performs denoising on the sinogram. However, more generally the trained DL network learns the image processing function that enables the filtered sinograms to most closely match the target sinograms. Thus, the trained DL network is not limited to denoising, but can also perform functions of edge enhancement and/or artifact suppression on the sinogram, if those functions result in the filtered/network-processed sinogram more closely matching the target sinogram. However, for simplicity and brevity the discussion refers to the DL network as performing the function of denoising, rather than mentioning a long list of functions performed to better match the target sinograms.

Figure 1:
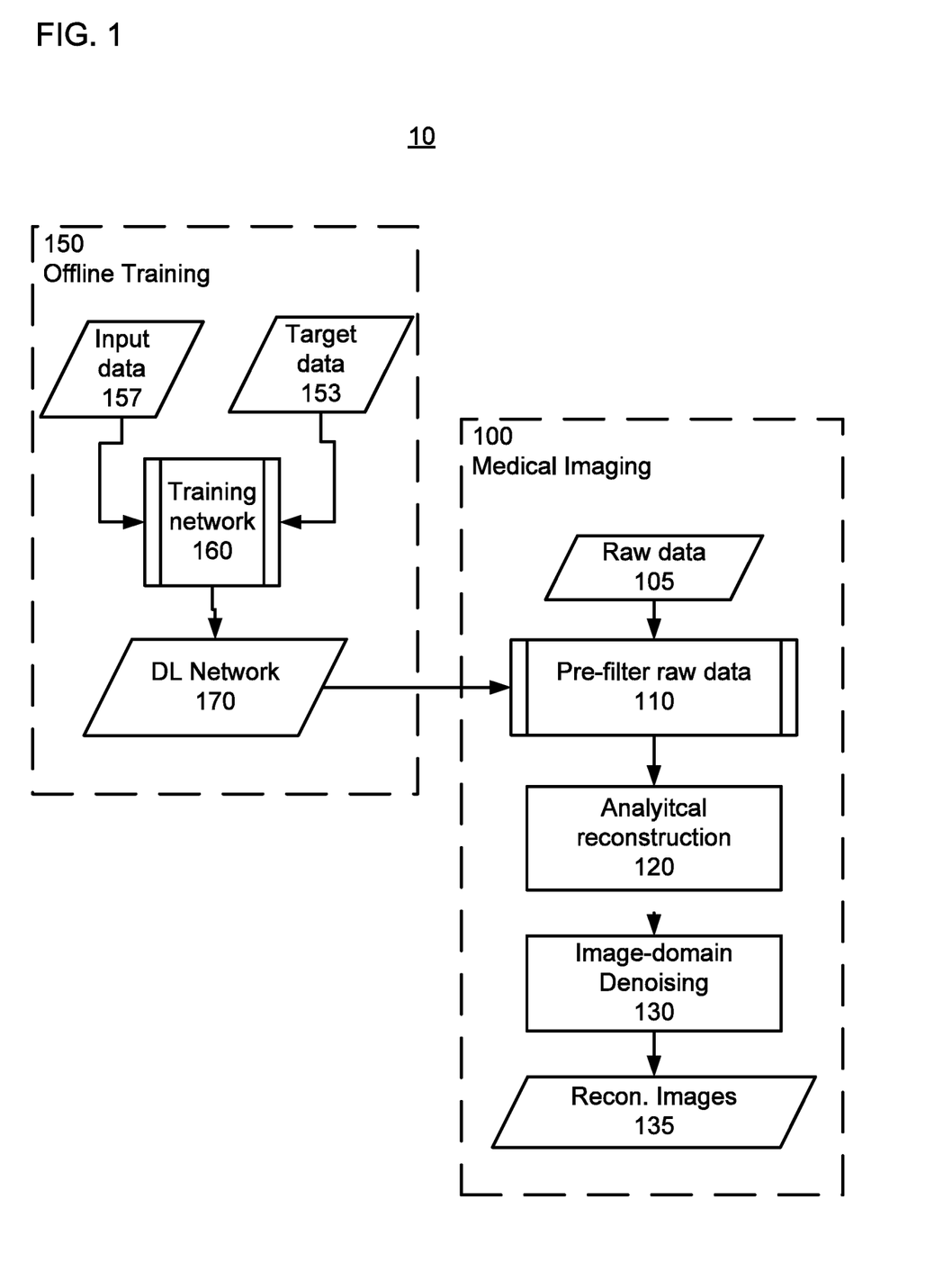
FIG. 1 shows a flow diagram of a method of training a deep learning (DL) network and then using the DL network to perform analytical computed tomography (CT) image reconstruction, according to one implementation.

Referring now to the drawings, wherein like reference numerals designate identical or corresponding parts throughout the several views, FIG. 1 shows a flow diagram for a non-limiting example of a method that trains and uses a DL neural network 170 to perform data-domain corrections of CT projection data (e.g., sinogram restoration, denoising, smoothing, and/or artifact correction). Method 10, as illustrated in FIG. 1, uses the DL network 170 to learn how to optimal filter raw data 105 (i.e., a sinogram), and then performs an analytical reconstruction step (e.g., back-projection) to reconstruct a CT image from the DL-network-filtered data. Method 10 includes two parts: (i) an offline training process 150 and (ii) a medical imaging process 100. That is, process 150 trains the DL network 170, and process 100 uses the trained DL network 170 to filter the raw data 105 in the projection domain, thereby generating high-quality images 135 with reduced noise and artifacts.

In certain implementations, the network 170 includes a convolutional neural network (CNN) in which series of convolution, batch normalization, and rectified linear unit network layers are performed.

The network 170 is trained using process 160. In process 160, a loss function is used to iteratively adjust/optimize parameters of the DL network 170 (e.g., the parameters of the DL network 170 can include weighting coefficients connecting network layers, and activation functions/potentials of nodes within the layers). The optimization of the network parameters continues until stopping criteria are satisfied (e.g., a stopping criterion can be whether the value of the loss function converged to a predefined threshold) to generate the trained network 170.

Figure 2:
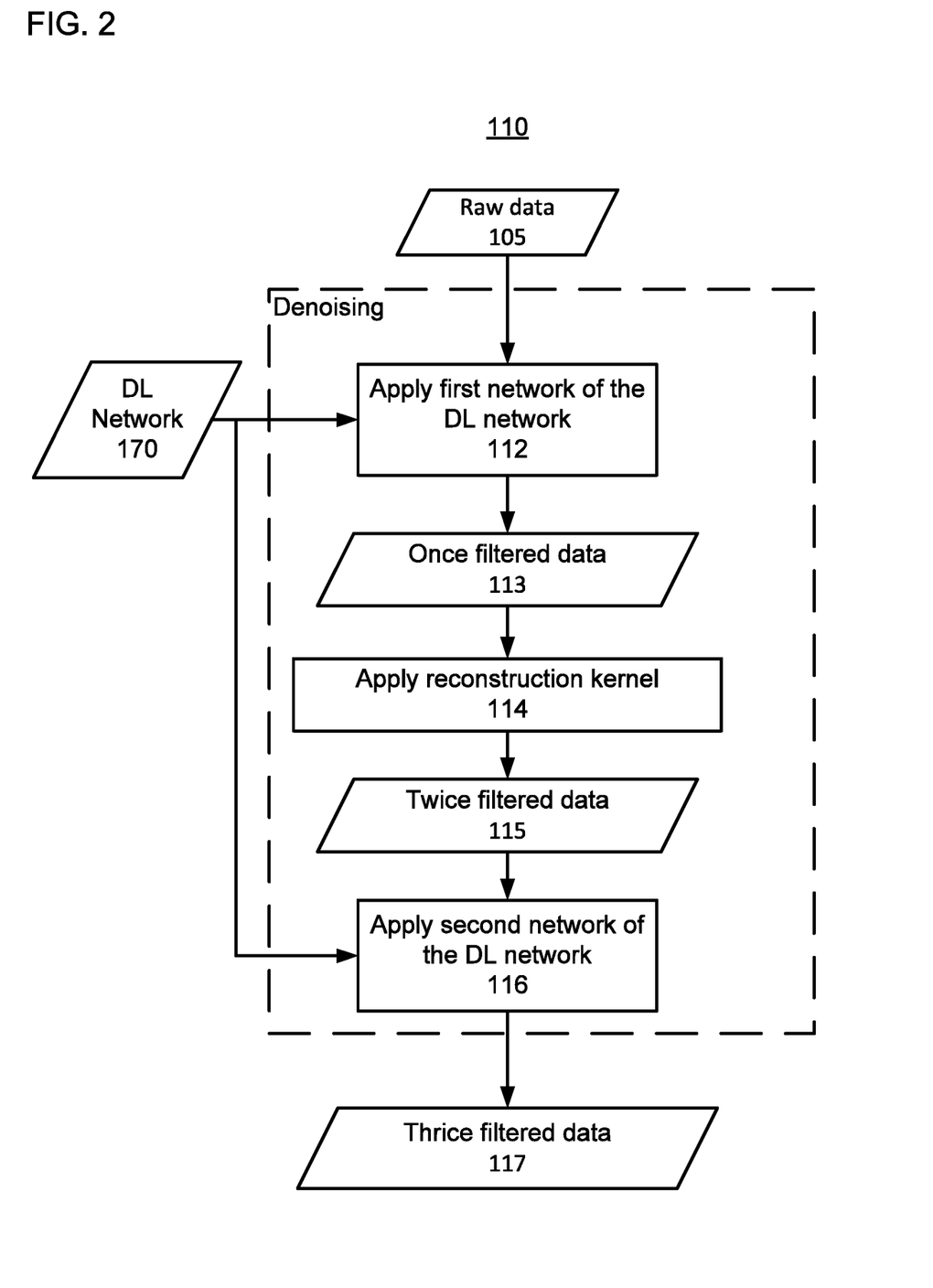
FIG. 2 shows a flow diagram of the process to filter a sinogram prior to an analytical reconstruction step, according to one implementation.

The loss function compares target data 153 to an output generated by applying the input data 157 to a current version of the DL network 170. For example, the input data can include noisy projection data in the sinogram/data domain for respective CT scans, and the target data can include low-noise (i.e., less noise than the input data) projection data in the sinogram/data domain for the same respective CT scans. Further, the target data are filtered using a predefined reconstruction kernel (e.g., a ramp filter) because, as shown in FIG. 2 at step 114, the process/filtering performed by the DL network 170 on the input data includes filtering using a reconstruction kernel.

For a given CT scan, each low-quality (e.g., noisy) sinogram of the input data forms a pair with the corresponding high-quality, reconstruction-kernel-filtered sinogram. In one implementation, the low-quality (e.g., noisy) sinogram is generated using a low-dose CT scan, and the high-quality (e.g., noise-reduced) sinogram is generated using a high-dose CT scan. These scans can be performed on a phantom, for example.

Applying a low-quality sinogram from the input data to the current version of the DL network 170 and to the reconstruction-kernel filtering generates an output from the network that is supposed to be a DL-network-filtered version of the low-quality sinogram (i.e., a filtered sinogram). The DL network 170 is trained by iteratively adjusting the network coefficients in the DL network 170 to minimize the difference between the DL-network-filtered sinogram output from the network 170 and the high-quality sinogram from the target data 153. The training of the network 170 is determined to be complete when the difference is minimized between the target data and the output from the DL network 170. The question of whether or not this difference has been sufficiently minimized is resolved based on one or more predetermined stopping criteria of process 160. Once the stopping criteria have been satisfied, the trained network 170 can then be stored and then later recalled to be used in the medical imaging process 100.

In alternative implementations, the DL network 170 is implemented as a residual network (ResNet). In this case, the method described herein can denoise an image by treating the noise as an additive residue that can be directly removed from the low-quality sinogram. This is achieved by treating the target data as being the noise/artifact itself (e.g., the difference between low-quality sinogram and the high-quality sinogram). Thus, when a low-quality sinogram is applied to the neural network, the network outputs an image representing the noise/artifact. Then the corrected sinogram can be generated by subtracting the network output (the noise/artifact) from the low-quality sinogram to generate the corrected sinogram.

In method 10, a loss function is used to iteratively adjust network coefficients (e.g., weights and biases of convolutional and pooling layers) of the DL network 170 until stopping criteria are satisfied (e.g., convergence of the parameters to a predefined threshold) to generate the trained network 170. The loss function compares high-quality data 153 to results of a current version of the DL network 170 to which input data 157 is applied.

As discussed above, CT image reconstruction is only one non-limiting illustrative example. Another example is positron emission tomography (PET) imaging. In the case PET imaging, sinograms can be generated for positron emission data, and sinogram denoising/restoration can be applied to the positron emission data using method 10. For example, method 10 includes training a DL network 170 and applying a low-quality (e.g., noisy) PET sinogram (i.e., raw data 105) to the trained network 170 to generate a high-quality PET sinogram.

In the case of PET imaging, the high- and low-quality data are accumulated over scans having long and short time durations, respectively. In general, the signal-to-noise ratio (SNR) is smaller for sinograms accumulated over shorter time durations. Accordingly, the target data 153 (e.g., high-quality sinograms) can be generated using all of the coincidence counts from a full-length PET scan to generate the highest possible SNR for the sinogram. On the other hand, the low-quality input data 157 can be generated using a partial subset of coincidence counts selected from the full dataset (e.g., using the data from only half of the full-length PET scan), resulting in a noisier sinogram (e.g., a $\sqrt{2}$ smaller SNR).

Returning to FIG. 1, process 100 is performed by obtaining raw data, e.g., by performing a CT scan to generate CT projections at a series of view angles (i.e., a low-quality sinogram). For example, the sinogram can be performed using a low-dose CT scan to generate the raw data 105.

In process 110 of process 100, the raw data 105 is filtered by applying the raw data 105 to the trained DL network 170. The DL network 170 then outputs a DL-network-filtered sinogram. A more detailed description of process 110 is provided below with reference to FIG. 2.

In step 120 of process 100, a CT image is reconstructed from the DL-network-filtered sinogram. Most often, the analytical reconstruction performed using back-projection. More generally, various methods can be used to perform analytical reconstruction, including the Feldkamp Davis Kress (FDK) method, the generalized FDK method, a rebinning FBP method, an n-Pi method, a Pi-slant method, Katsevich's exact method, an adaptive multiple plane reconstruction (AMPR) method, an advanced single-slice rebinning (ASSR), a weigthed FBP method, and an Adaptive Iterative Dose Reduction 3D (AIDR 3D) method.

In step 130 of process 100, additional image-domain denoising is performed. This step is optional, and can be omitted in some implementations.

Example denoising methods include linear smoothing filters, anisotropic diffusion, non-local means, or nonlinear filters. Linear smoothing filters remove noise by convolving the original image with a convolution kernel that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, a reconstructed image 135 is output having good image quality, and the reconstructed image 135 can be displayed to a user or stored for later use.

FIG. 2 show a flow diagram for a non-limiting example of process 110. This process shows two steps (i.e., steps 112 and 116) in which DL networks are used to filter the sinogram. The first DL-network step (i.e., step 112) uses a DL network to filter the sinogram before the reconstruction kernel filtering, and the second DL-network step (i.e., step 116) uses another DL network to filter the sinogram after the reconstruction kernel filtering. The first DL-network step (i.e., step 112) is optional and can be omitted in certain implementations. The DL networks for both step 112 and 116 can be thought of as part of DL network 170. Additionally, applying the reconstruction kernel at step 114 can also be thought of as part of DL network 170. However, step 114 does not include adjustable weighting coefficients that are optimized during the training process 160. Accordingly, FIG. 2 does not show step 114 receiving an input from DL network 170. Both steps 112 and 116 can be implemented as ResNets.

In step 112, the raw data 105 is applied to a first network of DL network 170, generating the once-filtered data 113.

In step 114, the once-filtered data 113 is filtered using the reconstruction kernel, generating the twice-filtered data 115. For example, in the spatial domain, the once-filtered data 113 can be convolved with the reconstruction kernel. Various types of reconstruction kernels can be used, as discussed below. In general, the same reconstruction kernel used to filter the once-filtered data 113 in step 114 is also used to prepare the target data used to train DL network 170.

In step 116, the twice-filtered data 113 is applied to a second network of DL network 170, generating the thrice-filtered data 117. In the training process 160, the same process as used in process 110 to generate the thrice-filtered data 117 from the raw data 105 is also used to generate output sinograms from the input data, and then compare, using the loss function, the output sinograms to the target data.

Often the reconstruction kernel is a ramp filter, but other variations can be used with departing from the spirit of method 10. Generally, the reconstruction kernel is a high pass filter that applies reduced weights to low frequencies that cause blurring to appear in the image. In frequency domain, that ramp filter mathematical function is given by $$H_R(k_x, k_y) = \sqrt{k_x^2 + k_y^2},$$

wherein $k_x$, and $k_y$ are the spatial frequencies.

The ramp filter is a compensatory filter as it eliminates the star artifact resulting from simple backprojection. Because the blurring appears in the trans-axial plane, the filter, is only applied in that plane. The ramp filter is linearly proportional to the spatial frequency. Generally, high-pass filters, like the ramp filter, sharpen the edges of the image (areas in an image where the signal changes rapidly) and enhance object edge information. A disadvantage of high pass filtering is the amplification of statistical noise present in the measured counts. In order to reduce the amplification of high-frequencies the ramp filter can be combined with a low-pass filter (e.g., a windowing function) to make the reconstruction kernel.

To reduce or remove statistical noise in a CT image the ramp filter can be combined with various low-pass/smoothing filters. Low-pass filters are characterized mainly by two parameters—the "cut-off frequency" and the "Order" (or the "Power"). The cut-off frequency (or roll-off frequency) defines the frequency above which the noise is eliminated. The filter function is defined to be zero for all frequencies above cut-off frequency. The value of the cut-off frequency determines how the filter will affect both image noise and resolution. A high cut-off frequency will improve the spatial resolution and therefore much detail can be seen but the image will remain noisy. A low cut-off frequency will increase smoothing but will degrade image contrast in the final reconstruction. The parameter Order controls the slope of the filter function and characterizes the steepness of the roll off. A high order will result in a sharp fall.

The ramp filter can be combined with one of several low-pass filters, a few of which are the Butterworth filter, the Hanning filter, the Hamming filter, the Parzen Filter, the Shepp-Logan filter. Further, Metz and Wiener are two types of resolution recovery filters that have been used in the reconstruction kernel. These low-pass filters are often referred to as windows, and the combination of a low-pass filter with a ramp filter can be referred to as a windowed ramp filter. Appropriate choice for which low-pass filter to use and the cut-off frequency among other parameters can depend on the geometry of the CT scanner and the detector array (e.g., the pixel pitch, the cone/fan-beam angle, and the point spread function of the X-rays). Common combinations of low-pass filters with the ramp filter are referred to by abbreviated names. For example, a rectangle function with the ramp filter is referred to as a Ram-Lak filter. The Shepp-Logan filter is another combination that can be used.

In certain implementations, the first and second networks of the DL network 170 used in steps 112 and 116 are a convolution neural network (CNN). The CNN can be a network that directly generates local small sized filters, e.g., $$y_i = \sum_{j \in \text{Neighbor of } i} w_{ij} x_j$$

wherein $w_{ij}$ is the filter on the ith pixel.

Now a more detailed description of training a DL network is provided (e.g., process 160). This description is illustrated using the example of the target data 153 being the high-quality sinograms and the input data 157 being low-quality sinograms.

Figure 3:
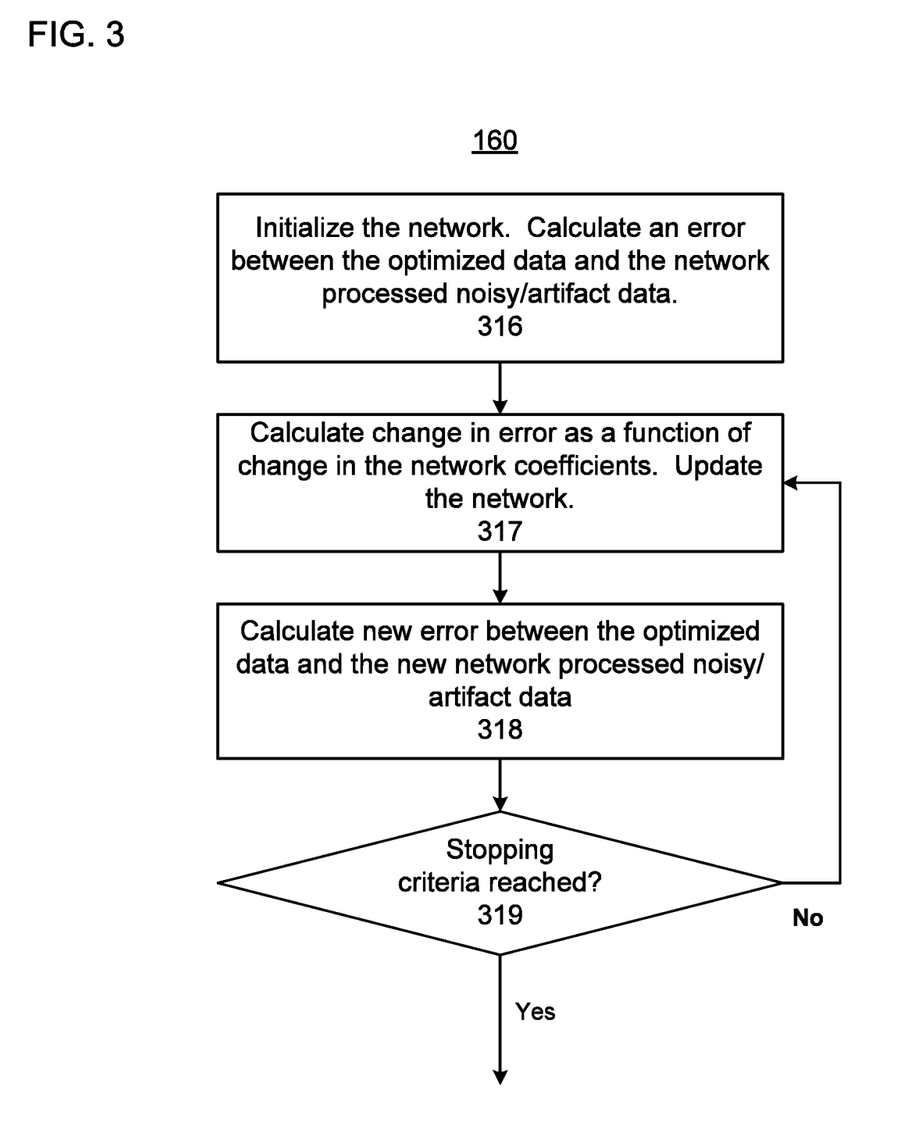
FIG. 3 shows a flow diagram of the process to train the DL network by iteratively adjusting coefficients of the DL network to optimize a loss-error function, according to one implementation.

FIG. 3 shows a flow diagram of one implementation of the training process 160. In process 160, input data 157 (e.g., low-quality sinograms) and target data 153 (e.g., high-quality sinograms) are used as training data to train a DL network 170, resulting in the DL network 170 being output from step 319 of process 160. The offline DL training process 160 trains the DL network 170 using a large number of input sinograms 157 that are paired with corresponding target sinograms 153 to train the DL network 170 to produce DL-network-filtered sinograms resembling the target sinograms 153 from the input sinograms 157.

In process 160, a set of training data is obtained, and the network 170 is iteratively updated to reduce the error (e.g., the value produced by a loss function). The DL network infers the mapping implied by the training data, and the cost function produces an error value related to the mismatch between the target sinograms 153 and the result produced by applying a current incarnation of the DL network 170 to the input sinograms 157. For example, in certain implementations, the cost function can use the mean-squared error to minimize the average squared error. In the case of a of multilayer perceptrons (MLP) neural network, the back-propagation algorithm can be used for training the network by minimizing the mean-squared-error-based cost function using a (stochastic) gradient descent method.

In step 316 of process 160, an initial guess is generated for the coefficients of the DL network 170. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 316 through 319 of process 160 provide a non-limiting example of an optimization method for training the DL network 170.

An error is calculated (e.g., using a loss function or a cost function) to represent a measure of the difference (e.g., a distance measure) between the target sinograms 153 (i.e., ground truth) and input sinograms 157 after applying a current version of the network 170. The error can be calculated using any known cost function or distance measure between the image data, including those cost functions described above. Further, in certain implementations the error/loss function can be calculated using one or more of a hinge loss and a cross-entropy loss.

In certain implementations, the training is performed by minimizing the following loss function $$\hat{\theta} = \arg\min_{\theta} \frac{1}{N} \sum_n L(\overline{y}^{(n)}, f(y^{(n)} | \theta, h)) + \beta R(h)$$

where $\theta$ are the adjustable weighting coefficients of the DL network 170, h are the non-adjustable parameters (e.g., parameters selected by a user, such as the choice of reconstruction kernel), $y^{(n)}$ represents the nth input sinogram, $\overline{y}^{(n)}$ represents the nth target sinogram. The number N is the total number of training projections. In certain implementations, the following weighted mean absolute error loss function is used $$L(\bar{y}, y) = \sum_j d_j |y_j - y_j|$$

wherein $d_j$ is the weight which has the form $$d_j = \bar{y}_j^p$$

with p being a scalar. The choice of this weight is inspired by the statistical mean estimation method where $d_j$ is often necessarily chosen to be the inverse of data noise variance. To handle the overfitting issue an additional regularization R on h is used, which is given by R (h)=$\Sigma_j h_j$. The regularization strength can be tuned thru the parameter $\beta$.

In certain implementations, the network 170 is trained using backpropagation. Backpropagation can be used for training neural networks and is used in conjunction with gradient descent optimization methods. During a forward pass, the algorithm computes the network's predictions based on the current parameters $\Theta$. These predictions are then input into the loss function, by which they are compared to the corresponding ground truth labels (i.e., the high-quality data 153). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

In certain implementations, the image processing in steps 112-116 are considered as being the DL network for backpropagation. However, only the weighting coefficients in the CNN implemented in steps 112 and 116 are allowed to be changed. That is, the weighting coefficients in the CNN can be adjusted to generate a better match with the target sinograms, but the parameters for performing step 114 do not change. In this sense, the entirety of steps 112-116 can be considered as the DL network, even though only the weighting coefficients in the network of steps 112 and 116 are being adjusted by the training process.

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 3, step 317 of process 160 determines a change in the error as a function of the change in the network can be calculated (e.g., an error gradient), and this change in the error can be used to select a direction and step size for a subsequent change to the weights/coefficients of the DL network 170. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 317 of process 160, a new set of coefficients are determined for the DL network 170. For example, the weights/coefficients can be updated using the changed calculated in step 317, as in a gradient descent optimization method or an over-relaxation acceleration method.

In step 318 of process 160, a new error value is calculated using the updated weights/coefficients of the DL network 170.

In step 319, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 160 will continue back to the start of the iterative loop by returning and repeating step 317 using the new weights and coefficients (the iterative loop includes steps 317, 318, and 319). When the stopping criteria are satisfied the training process performed in process 160 is completed.

Figure 4A:
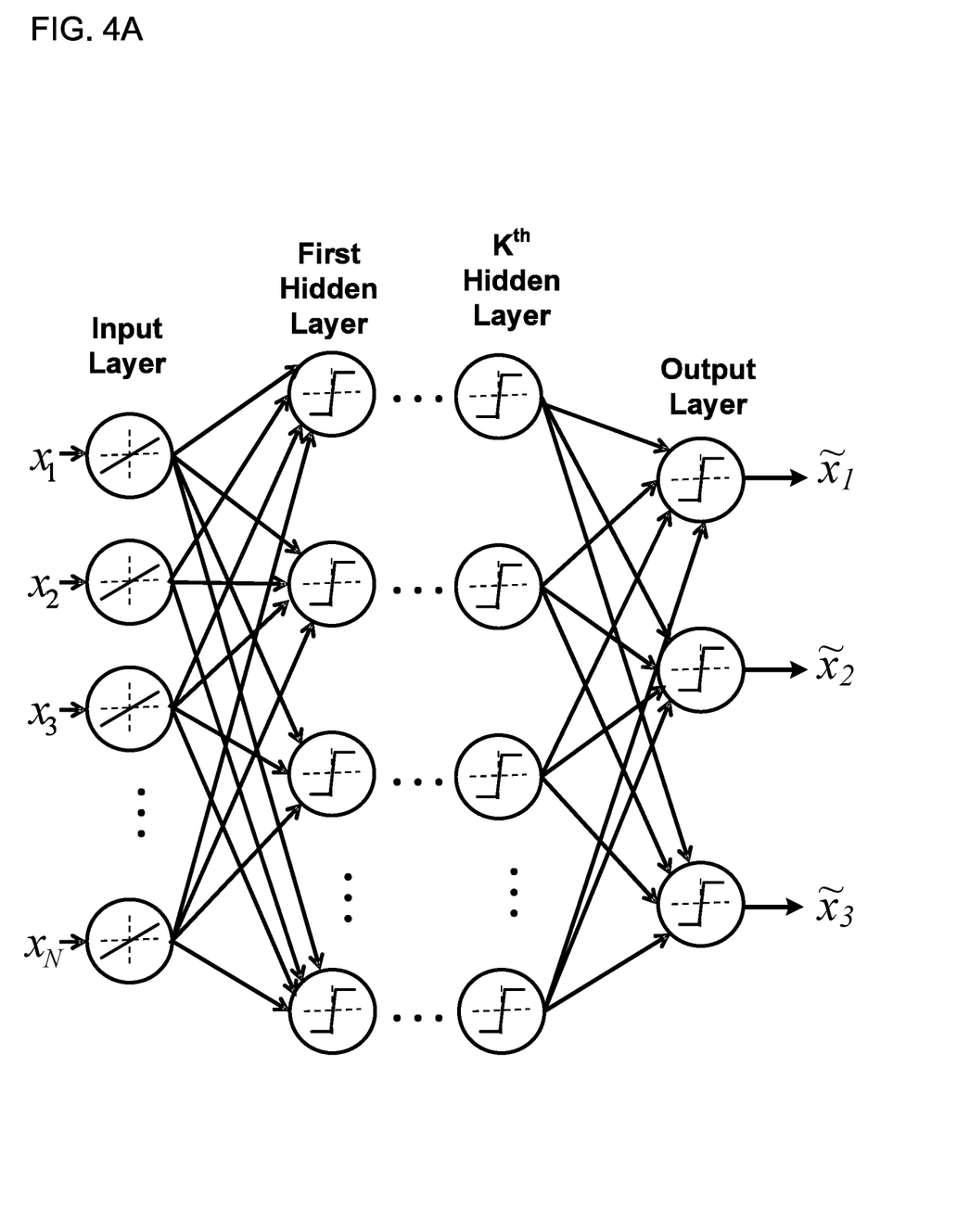
FIG. 4A shows an example of a DL network, according to one implementation.
Figure 4B:
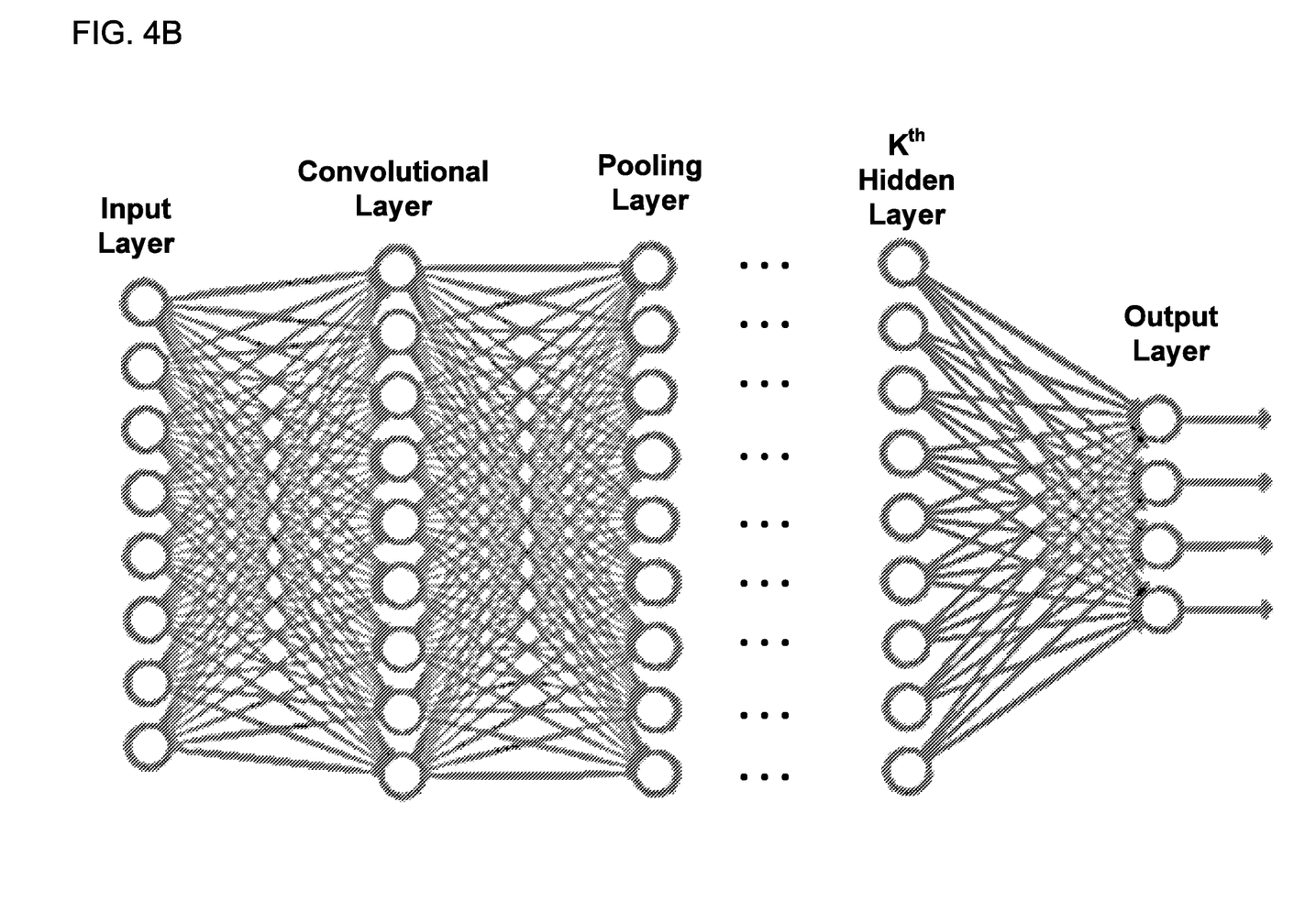
FIG. 4B shows an example of a type of DL network referred to as a convolutional neural network (CNN), according to one implementation.

FIGS. 5A and 5B show various examples of the interconnections between layers in the DL network 170. The DL network 170 can include fully connected, convolutional, and the pooling layer, all of which are explained below. In certain preferred implementations of the DL network 170, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 170 can also incorporate batch normalization, as also exemplified in the first and second examples discussed above.

FIG. 4A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 4A. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 4A (and similarly in FIG. 4B), the neurons (i.e., nodes) are depicted by circles around a threshold function. For the non-limiting example shown in FIG. 4A, the inputs are depicted as circles around a linear function, and the arrows indicate directed connections between neurons. In certain implementations, the DL network 170 is a feedforward network.

FIG. 4B shows a non-limiting example in which the DL network 170 is a convolutional neural network (CNN). CNNs are type of ANN that has beneficial properties for image processing, and, therefore, have specially relevancy for the applications of image denoising. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

Figure 5:
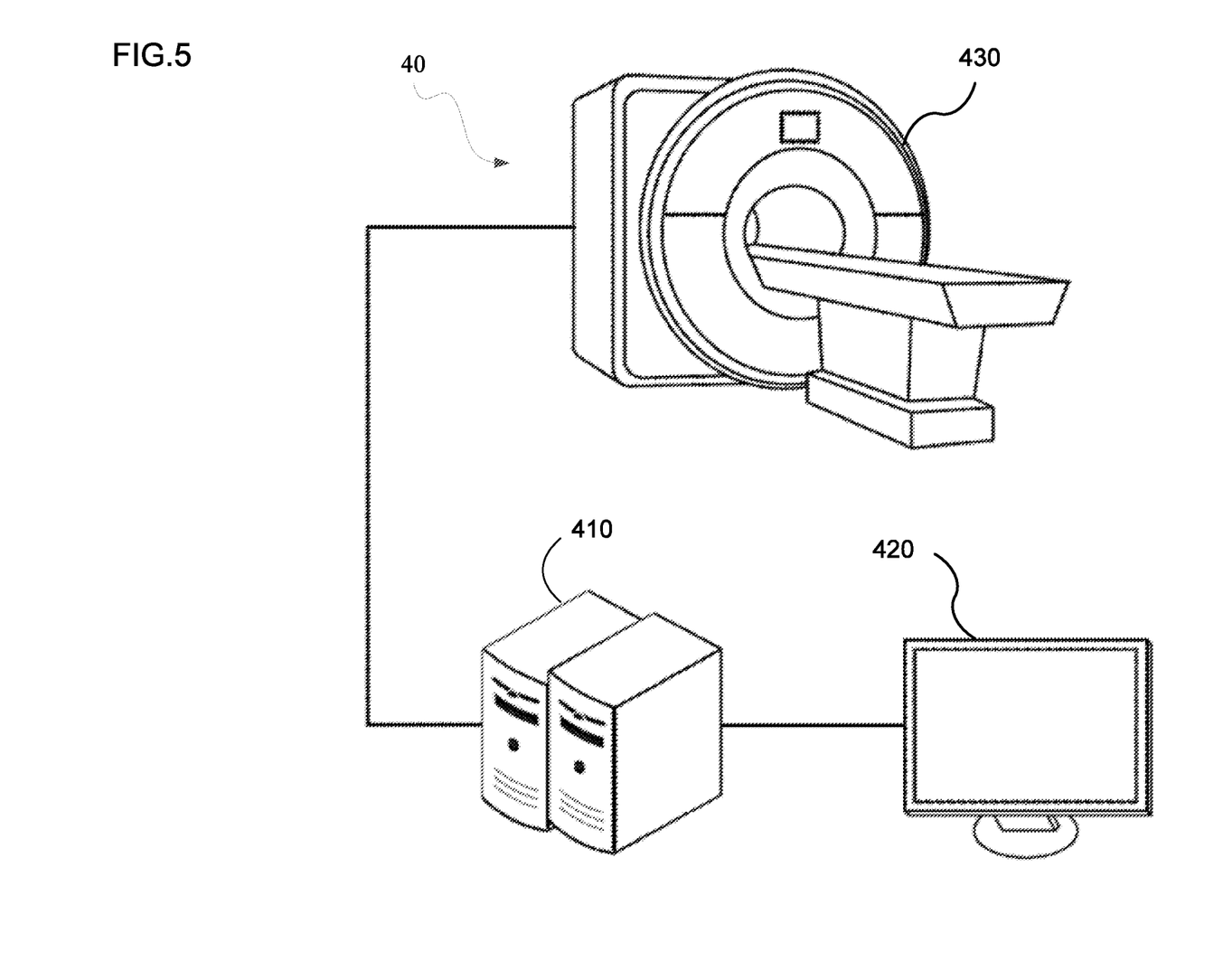
FIG. 5 shows diagram of a medical imaging system, according to one implementation.

FIG. 5 illustrates an example embodiment of a medical-imaging system 40. The medical-imaging system 40 includes at least one scanning device 430; one or more image-generation devices 410, each of which is a specially-configured computing device (e.g., a specially-configured desktop computer, a specially-configured laptop computer, a specially-configured server); and a display device 420.

The scanning device 430 is configured to acquire scan data by scanning a region (e.g., area, volume, or slice) of an object (e.g., a patient). The scanning modality may be, for example, computed tomography (CT), positron emission tomography (PET), and/or single photon emission CT (SPECT). The one or more image-generation devices 410 obtain scan data from the scanning device 430 and generate an image of the region of the object based on the scan data. After the one or more image-generation devices 410 generate the image, the one or more image-generation devices 410 send the image to the display device 420, which displays the image.

Figure 6:
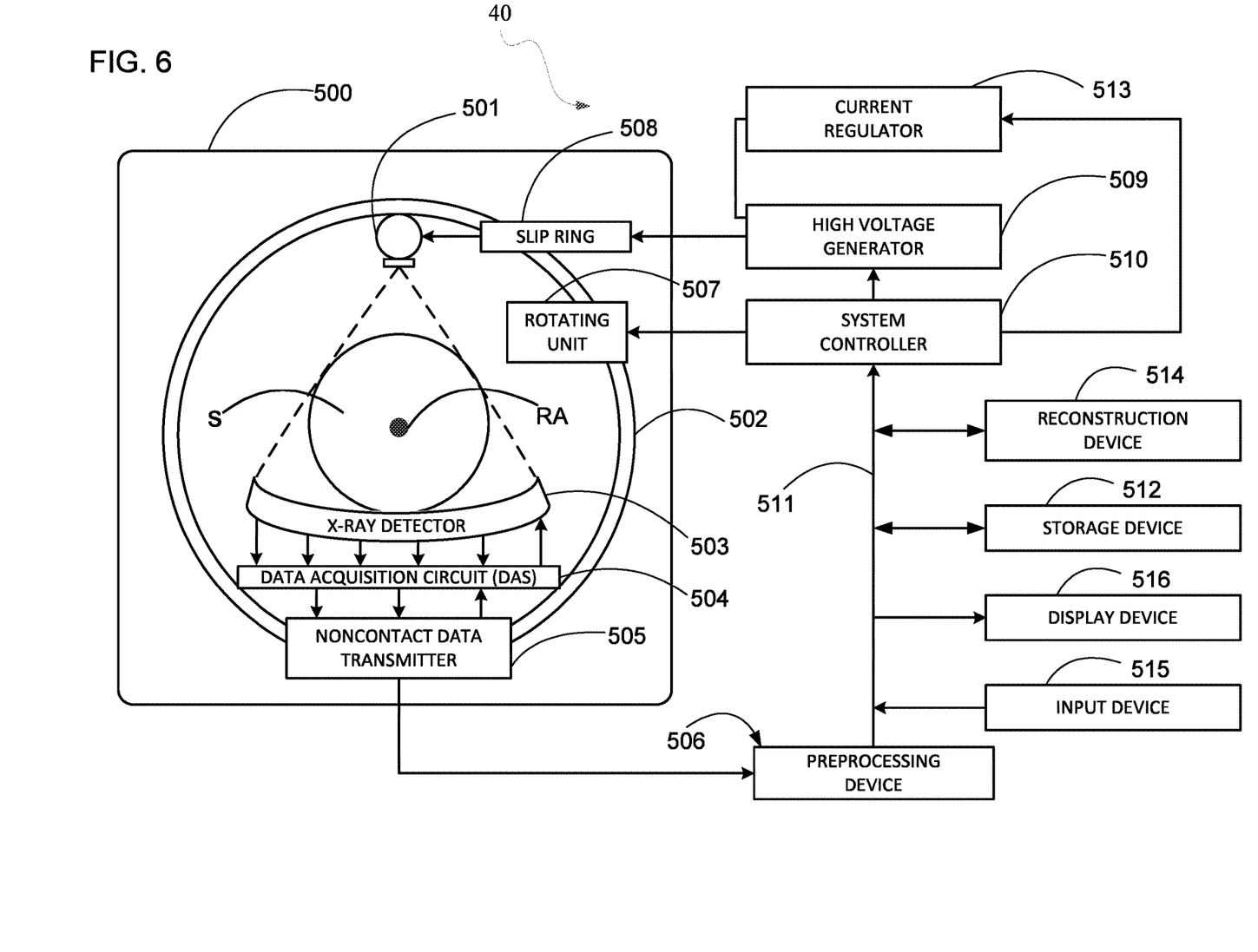
FIG. 6 shows a schematic diagram of an X-ray CT scanner, according to one implementation.

FIG. 6 illustrates in implementation in which the medical-imaging system 40 includes a CT scanner. As shown in FIG. 7, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal.

The above-described data is sent to a preprocessing circuitry 506, which is housed in a console outside the radiography gantry 500 through a non-contact data transmitter 505. The preprocessing circuitry 506 performs certain corrections, such as sensitivity correction on the raw data. A storage 512 stores the resultant data, which is also called projection data at a stage immediately before reconstruction processing. The storage 512 is connected to a processing circuitry 510 through a data/control bus 511, together with a reconstruction device 514, input interface 515, and display 516. The processing circuitry 510 controls a current regulator 513 that limits the current to a level sufficient for driving the CT system.

The detectors are rotated and/or fixed with respect to the patient among various generations of the CT scanner systems. In one implementation, the X-ray tube 501 and the X-ray detector 503 are diametrically mounted on the annular frame 502 and are rotated around the object OBJ as the annular frame 502 is rotated about the rotation axis RA.

The storage 512 can store the measurement value representative of the irradiance of the X-rays at the X-ray detector unit 503. Further, the storage 512 can store a dedicated program for executing method 10.

The reconstruction circuitry 514 can execute various steps of method 10. Further, reconstruction circuitry 514 can execute pre-reconstruction processing image processing such as volume rendering processing and image difference processing as needed.

The pre-reconstruction processing of the projection data performed by the preprocessing circuitry 506 can include correcting for detector calibrations, detector nonlinearities, and polar effects, for example.

Post-reconstruction processing performed by the reconstruction circuitry 514 can include filtering and smoothing the image, volume rendering processing, and image difference processing as needed. The image reconstruction process can implement various steps of method 10. The reconstruction circuitry 514 can use the memory to store, e.g., projection data, reconstructed images, calibration data and parameters, and computer programs.

The various circuitry (e.g., the reconstruction circuitry 514 and preprocessing circuitry 506) can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 512 can be non-volatile, such as ROM, EPROM, EEPROM or FLASH memory. The storage 512 can also be volatile, such as static or dynamic RAM, and a processor, such as a microcontroller or microprocessor, can be provided to manage the electronic memory as well as the interaction between the FPGA or CPLD and the memory.

In one implementation, the reconstructed images can be displayed on a display 516. The display 516 can be an LCD display, CRT display, plasma display, OLED, LED or any other display known in the art.

Figure 7A:
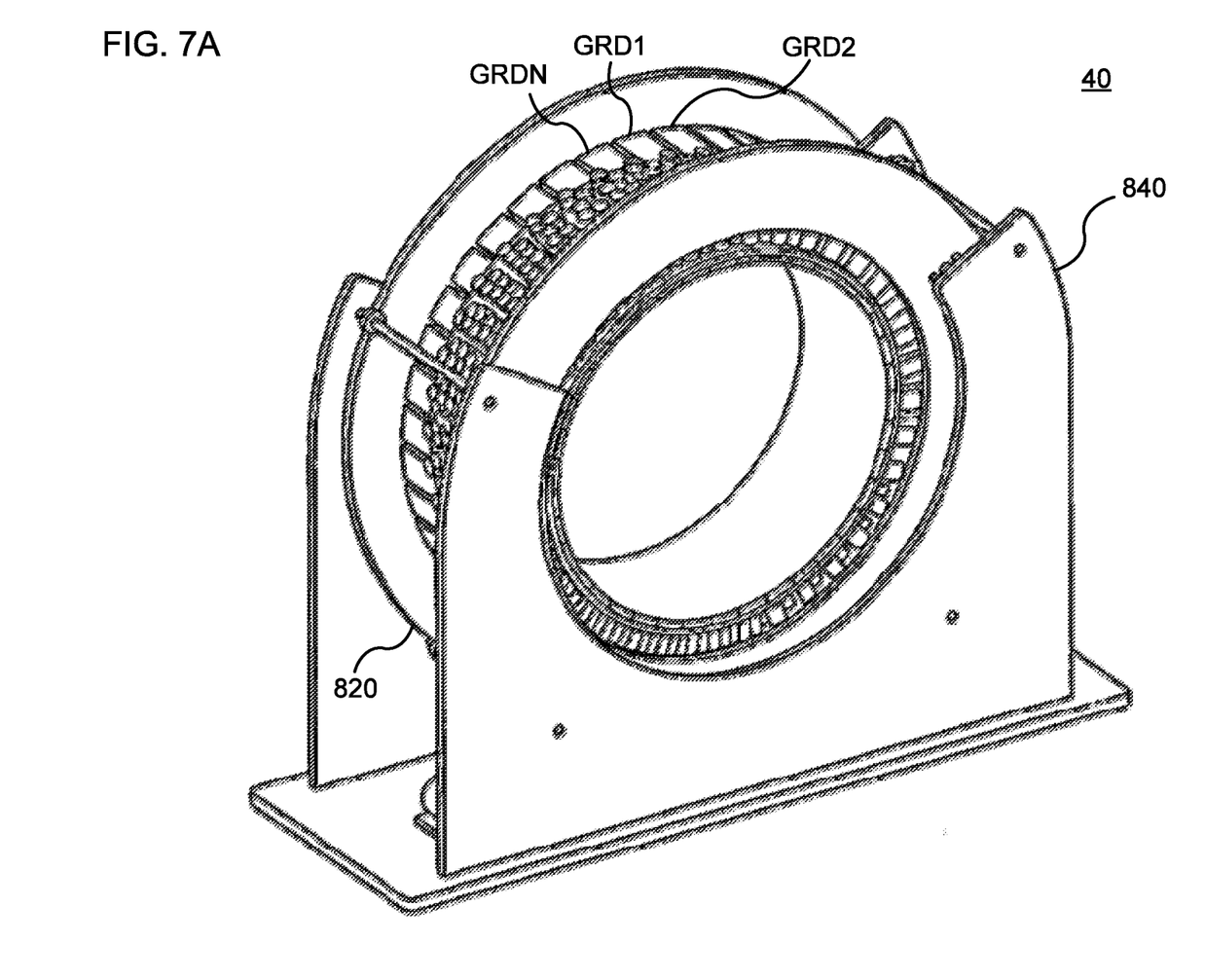
FIG. 7A shows a perspective of a positron emission tomography (PET) scanner, according to one implementation.
Figure 7B:
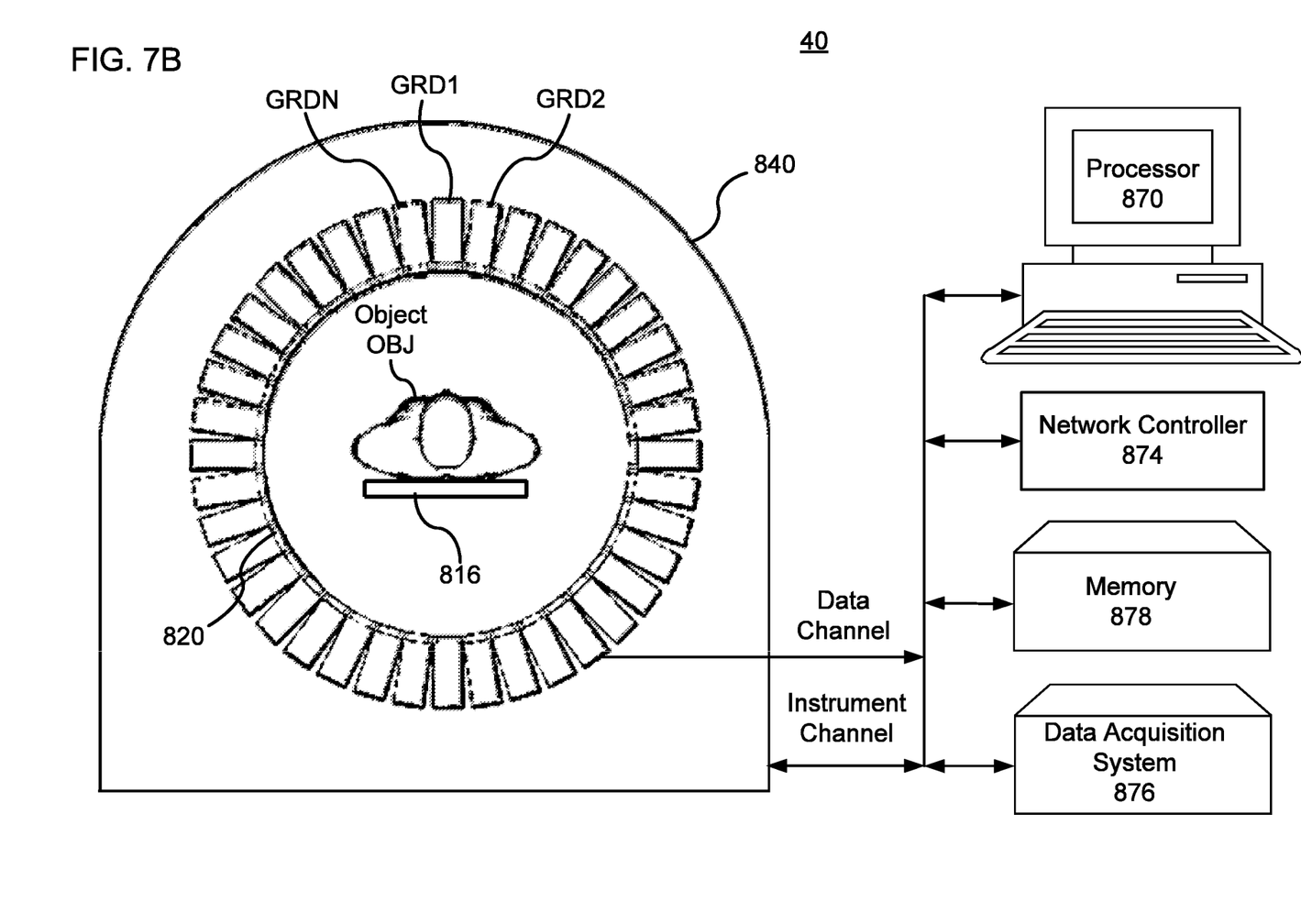
FIG. 7B shows a schematic diagram of the PET scanner, according to one implementation.

FIGS. 9A and 9B illustrates in implementation in which the medical-imaging system 40 includes a PET scanner that can implement the method 10. The PET scanner includes a number of gamma-ray detectors (GRDs) (e.g., GRD1, GRD2, through GRDN) that are each configured as rectangular detector modules.

Each GRD can include a two-dimensional array of individual detector crystals, which absorb gamma radiation and emit scintillation photons. The scintillation photons can be detected by a two-dimensional array of photomultiplier tubes (PMTs) or silicon photomultipliers (SiPMs). A light guide can be disposed between the array of detector crystals and the photodetectors.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 9B shows a schematic view of a PET scanner having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 9A and 8B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 9B shows an example of the arrangement of the PET scanner, in which the object OBJ to be imaged rests on a table 816 and the GRD modules GRD1 through GRDN are arranged circumferentially around the object OBJ and the table 816. The GRDs can be fixedly connected to a circular component 820 that is fixedly connected to the gantry 840. The gantry 840 houses many parts of the PET imager. The gantry 840 of the PET imager also includes an open aperture through which the object OBJ and the table 816 can pass, and gamma-rays emitted in opposite directions from the object OBJ due to an annihilation event can be detected by the GRDs and timing and energy information can be used to determine coincidences for gamma-ray pairs.

In FIG. 9B, circuitry and hardware is also shown for acquiring, storing, processing, and distributing gamma-ray detection data. The circuitry and hardware include: a processor 870, a network controller 874, a memory 878, and a data acquisition system (DAS) 876. The PET imager also includes a data channel that routes detection measurement results from the GRDs to the DAS 876, a processor 870, a memory 878, and a network controller 874. The data acquisition system 876 can control the acquisition, digitization, and routing of the detection data from the detectors. In one implementation, the DAS 876 controls the movement of the bed 816. The processor 870 performs functions including reconstructing images from the detection data, pre-reconstruction processing of the detection data, and post-reconstruction processing of the image data, as discussed herein.

The processor 870 can be configured to perform various steps of method 10 described herein and variations thereof. The processor 870 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 870 can execute a computer program including a set of computer-readable instructions that perform various steps of method 10, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 878 can be a hard disk drive, CD-ROM drive, DVD drive, FLASH drive, RAM, ROM or any other electronic storage known in the art.

The network controller 874, such as an Intel Ethernet PRO network interface card from Intel Corporation of America, can interface between the various parts of the PET imager. Additionally, the network controller 874 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
circuitry configured to
obtain a radiation sinogram representing respective projection images at corresponding view angles, each of the projection images representing an intensity of radiation detected by a plurality of detectors,
acquire a first neural network and a second neural network,
apply the radiation sinogram to the second neural network to thereby output the radiation sinogram that has been filtered using the second neural network,
filter, using a reconstruction kernel, the radiation sinogram that has been filtered using the second neural network to thereby generate reconstruction-kernel filtered data,
apply the reconstruction-kernel filtered data to the first neural network to thereby output a filtered sinogram from the first neural network, and
perform analytic reconstruction on the filtered sinogram output from the first neural network to generate a computed tomography (CT) image, wherein the second neural network is trained using respective pairs of input sinograms and target sinograms, wherein (1) higher-noise sinograms are utilized as the input sinograms and (2) the target sinograms are generated by applying the reconstruction kernel to lower-noise sinograms corresponding to the higher-noise sinograms.

2. The apparatus according to claim 1, wherein the circuitry is further configured to perform analytic reconstruction on the filtered sinogram by back-projecting the filtered sinogram to reconstruct the CT image.

3. The apparatus according to claim 1, wherein the reconstruction kernel is a ramp filter.

4. The apparatus according to claim 1, wherein the circuitry is further configured to train the first neural network and the second neural network by
using the first neural network and the second neural network to generate an output sinogram from the respective input sinograms by
applying a given input sinogram to the second neural network, thereby generating a first output,
filtering the reconstruction kernel to the first output, thereby generating a second output, and
applying the second output to the first neural network, thereby generating a third output; and
training the first neural network and the second neural network by iteratively adjusting weighting coefficients of the first neural network and weighting coefficients of the second neural network to minimize a value of a loss function, the loss function measuring a disagreement between the third output and a target sinogram that corresponds to the given input sinogram used to generate the third output.

5. The apparatus according to claim 1, wherein the circuitry is further configured to train the first neural network by
obtain a training dataset comprising input sinograms paired with respective target sinograms,
using the first neural network to generate output sinogram from the respective input sinograms by
applying the reconstruction kernel to a given input sinogram, thereby generating a first output, and
applying the first output to the first neural network, thereby generating a second output; and
training the first neural network by iteratively adjusting weighting coefficients the first neural network to minimize a value of a loss function, the loss function measuring a disagreement between the second output and a target sinogram that corresponds to the given input sinogram used to generate the second output.

6. The apparatus according to claim 5, wherein the circuitry is further configured to train the first neural network using the training dataset, wherein
the input sinograms are acquired using a low-dose CT scan to obtain a low-dose sinogram as an input sinogram, and
the target sinograms are acquired using a CT high-dose scan to obtain a high-dose sinogram, which applies a higher dose than the CT low-dose scan, and
a predefined reconstruction kernel is applied to the high-dose sinogram to generate a target sinogram.

7. The apparatus according to claim 6, wherein the circuitry is further configured to obtain the training dataset wherein the target sinograms are acquired using as the predefined reconstruction kernel, which is applied to the high-dose sinogram, one of ramp filter, a Ram-Lak filter, a Shepp-Logan Filter, a cosine-windowed ramp filter, a Hamming-windowed ramp filter, and a windowed ramp filter based on a scanner geometry.

8. The apparatus according to claim 5, wherein the circuitry is further configured to apply the reconstruction kernel, wherein the reconstruction kernel, which applied to the input sinogram, is a same convolutional kernel as a predefined reconstruction kernel used to generate the target sinograms of the training dataset.

9. The apparatus according to claim 5, wherein the circuitry is further configured to train the first neural network using the training dataset, wherein
the input sinograms are acquired using a first configuration of an imaging scanner to obtain a first-configuration sinogram as an input sinograms, and
the target sinograms are acquired using a second configuration of an imaging scanner to obtain a second-configuration sinogram and then applying a predefined reconstruction kernel to the second-configuration sinogram to generate a target sinogram, the second-configuration sinogram producing a better quality image when filtered backprojection CT image reconstruction is performed than does the corresponding first-configuration sinogram.

10. The apparatus according to claim 9, wherein the circuitry is further configured to train the first neural network using the training dataset, wherein the first configuration of the imaging scanner used to acquire the input sinograms and the second configuration of the imaging scanner used to acquire the target sinograms differ with respect to one or more settings of a radiation source of the imaging scanner.

11. The apparatus according to claim 1, wherein the circuitry is further configured to apply the radiation sinogram to the first neural network, wherein the first neural network is a residual network.

12. The apparatus according to claim 1, wherein the circuitry is further configured to obtain radiation data, wherein the radiation data is one of X-ray computed tomography (CT) data, X-ray fluoroscopy data, gamma-ray positron emission tomography (PET), and single-photon emission CT data (SPECT).

13. The apparatus according to claim 1, the circuitry is further configured to apply the radiation sinogram to the second neural network, wherein the second neural network reduces noise in the radiation sinogram that has been filtered using the second neural network relative to the radiation sinogram.

14. The apparatus according to claim 1, wherein the circuitry is further configured to acquire the first neural network, wherein weighting coefficients of the first neural network and weighting coefficients have been trained using a training dataset that includes input data and target data, the input data comprising first training sinograms acquired using a first radiation dose, and the target data comprising second training sinograms acquired using a second radiation dose that is greater than the first radiation dose.

15. The apparatus according to claim 5, wherein the circuitry is further configured to train the neural network wherein the loss function includes a peak signal to noise ratio, a structural similarity index, and/or an lp-norm of a difference between the respective target sinograms and the filtered sinograms corresponding to the input sinograms.

16. The apparatus according to claim 1, wherein the radiation sinogram is X-ray CT projection data, and the apparatus further comprises:
an X-ray source configured to emit X-rays and configured to rotate around an object; and
a detector configured rotate and be opposite to the X-ray source across from the objection, the detector being further configured to receive the emitted X-rays from the X-ray source at a plurality of detector elements to generate projection data as the radiation sinogram, the projection data representing an intensity of the X-rays at the plurality of detector elements.

17. A method, comprising:
obtaining a radiation sinogram representing respective projection images at corresponding view angles, each of the projection images representing an intensity of radiation detected by a plurality of detectors;
acquiring a first neural network and a second neural network;
applying the radiation sinogram to the second neural network to thereby output the radiation sinogram that has been filtered using the second neural network,
filtering, using a reconstruction kernel, the radiation sinogram that has been filtered using the second neural network to thereby generate reconstruction-kernel filtered data;
applying the reconstruction-kernel filtered data to the filter neural network to thereby output a filtered sinogram from the second neural network; and
performing analytic reconstruction on the filtered sinogram output from the first neural network to generate a computed tomography (CT) image, wherein the second neural network is trained using respective pairs of input sinograms and target sinograms, wherein (1) higher-noise sinograms are utilized as the input sinograms and (2) the target sinograms are generated by applying the reconstruction kernel to lower-noise sinograms corresponding to the higher-noise sinograms.

18. A non-transitory computer-readable storage medium including executable instructions, which when executed by circuitry, cause the circuitry to perform the method according to claim 17.

19. The apparatus as claimed in claim 1, wherein the second neural network is trained for each kind of the reconstruction kernel.

20. The apparatus as claimed in claim 19, wherein the second neural network is trained using the following loss function $$\hat{\theta} = \underset{\theta}{\operatorname{argmin}} \frac{1}{N} \sum_n L(\bar{y}^{(n)}, f(y^{(n)}|\theta, h)) + \beta R(h),$$

where $\theta$ are adjustable weighting coefficients of network, h are non-adjustable parameters, $y^{(n)}$ represents the n-th input sinogram, $\bar{y}^{(n)}$ represents the n-th target sinogram, and "N" is a total number of training projections.

* * * * *